United States Patent
Clements et al.

(10) Patent No.: US 11,124,693 B2
(45) Date of Patent: Sep. 21, 2021

(54) HYDROXYALKYLURETHANE KINETIC HYDRATE INHIBITORS

(71) Applicant: Indorama Ventures Oxides LLC, The Woodlands, TX (US)

(72) Inventors: John H. Clements, The Woodlands, TX (US); Marek Pakulski, The Woodlands, TX (US); David C. Lewis, The Woodlands, TX (US)

(73) Assignee: Indorama Ventures Oxides LLC, The Woodlands, TX (US)

(*) Notice: Subject to any disclaimer, the term of this patent is extended or adjusted under 35 U.S.C. 154(b) by 71 days.

(21) Appl. No.: 16/340,699

(22) PCT Filed: Jan. 30, 2018

(86) PCT No.: PCT/US2018/015859
§ 371 (c)(1),
(2) Date: Apr. 10, 2019

(87) PCT Pub. No.: WO2018/160306
PCT Pub. Date: Sep. 7, 2018

(65) Prior Publication Data
US 2019/0375979 A1   Dec. 12, 2019

Related U.S. Application Data

(60) Provisional application No. 62/464,493, filed on Feb. 28, 2017.

(51) Int. Cl.
*C09K 8/524* (2006.01)
*C07D 319/06* (2006.01)

(52) U.S. Cl.
CPC ............ *C09K 8/524* (2013.01); *C07D 319/06* (2013.01)

(58) Field of Classification Search
None
See application file for complete search history.

(56) References Cited

U.S. PATENT DOCUMENTS

| | | | |
|---|---|---|---|
| 5,741,758 A | 4/1998 | Pakulski | |
| 5,817,898 A * | 10/1998 | Delion | ........... C10L 3/06 585/15 |
| 6,025,302 A | 2/2000 | Pakulski | |
| 6,331,508 B1 | 12/2001 | Pakulski | |
| 6,566,309 B1 * | 5/2003 | Klug | ........... C08G 65/33303 507/90 |
| 7,214,814 B2 | 5/2007 | Dahlmann et al. | |
| 7,232,609 B2 | 6/2007 | Ahmed et al. | |
| 7,253,138 B2 | 8/2007 | Dahlmann et al. | |
| 7,341,617 B2 | 3/2008 | Dahlmann et al. | |
| 7,968,500 B2 | 6/2011 | Pakulski et al. | |

(Continued)

OTHER PUBLICATIONS

Abrahamsen, E et al., Carbamate Polymers as Kinetic Hydrate Inhibitors, Energy Fuels 30 (10), pp. 9134-8140, 2016; abstact only.

(Continued)

*Primary Examiner* — John J Figueroa

(57) ABSTRACT

The present disclosure generally relates to hydroxyalkylurethanes obtained from the reaction of amines and alkylene carbonates and their use in gas hydrate inhibitor compositions to effectively inhibit gas hydrate formation in a crude hydrocarbon stream.

11 Claims, 2 Drawing Sheets

(56) References Cited

U.S. PATENT DOCUMENTS

| | | | |
|---|---|---|---|
| 7,989,553 B2* | 8/2011 | Birukov | C08G 59/56 |
| | | | 525/403 |
| 8,183,185 B2 | 5/2012 | Pakulski et al. | |
| 2002/0040160 A1* | 4/2002 | Clements | C07C 271/16 |
| | | | 560/157 |
| 2006/0237691 A1 | 10/2006 | Meier et al. | |
| 2010/0249337 A1* | 9/2010 | Birukov | C08G 59/4014 |
| | | | 525/408 |
| 2015/0148266 A1* | 5/2015 | Webber | F17D 1/16 |
| | | | 507/90 |

OTHER PUBLICATIONS

Guan, J et al., Progress in Study of Non-Isocyanate Polyurethane, Industrial & Enginn=eering Chemistry Research 50, pp. 6517-6527, 2011; p. 6518, Scheme 3.

\* cited by examiner

HYDROXYALKYLURETHANE KINETIC HYDRATE INHIBITORS

CROSS-REFERENCE TO RELATED APPLICATIONS

This application is the National Phase of International Application PCT/US2018/015859 filed Jan. 30, 2018 which designated the U.S., and which claims priority to U.S. App. Ser. No. 62/464,493 filed Feb. 28, 2017. The noted applications are incorporated herein by reference.

STATEMENT REGARDING FEDERALLY SPONSORED RESEARCH OR DEVELOPMENT

Not applicable.

FIELD OF THE INVENTION

The present disclosure relates to kinetic hydrate inhibitors, in particular hydroxyalkylurethanes, and their use in a variety of oil and gas applications including, but not limited to, gas hydrate inhibition in well drilling, completion, natural gas production, processing, transportation and storage.

BACKGROUND OF THE INVENTION

The formation of gas hydrates has long been recognized as a potential problem in the oil and gas industry. During recent years, the general trend within the industry to make more efficient designs and to minimize cost wherever possible has led to considerable effort to understand hydrate formation and methods to prevent or inhibit such formation.

Gas hydrates are solids that form from a combination of water and one or more hydrocarbon or non-hydrocarbon gases. In physical appearance, gas hydrates resemble packed snow or ice. In a gas hydrate, the gas molecules are "caged" within a crystal structure composed of water molecules. Sometimes gas hydrates are called "gas clathrates". Clathrates are substances having molecules of one compound completely "caged" within the crystal structure of another. Thus, gas hydrates are one type of clathrate.

Two broad techniques are generally used to overcome or control gas hydrate formation, namely thermodynamic and kinetic, which can be used alone or in conjunction. For the thermodynamic approach, there are a number of reported or attempted methods, including water removal, increasing temperature, decreasing pressure, addition of lower molecular weight alcohols and glycols to the fluid and/or a combination of these. For the kinetic approach, attempts have been made to (a) prevent the smaller hydrocarbon hydrate crystals from agglomerating into larger ones (known in the industry as an agglomeration inhibitor) and/or (b) inhibit, retard and/or prevent initial hydrocarbon hydrate crystal nucleation and/or crystal growth (known in the industry as a kinetic hydrate inhibitor).

Agglomeration inhibitors are typically quaternary ammonium or phosphonium salts, such as tributylhexadecylphosphonium bromide and tributylhexadecylammonium bromide. However, these compounds tend to have undesirable levels of toxicity, are poorly biodegradable and do not function well in water with relatively low salt concentrations (such as in some areas of the North Sea) and are therefore generally disfavored.

Kinetic efforts to control hydrates have included the use of different materials as inhibitors. For example, onium compounds having at least four carbon substituents have been used to inhibit the plugging of conduits by gas hydrates. Other examples of kinetic hydrate inhibitors include polyvinylpyrrolidone, copolymers of vinyl pyrrolidinone (e.g. with alphaolefins, vinyl caprolactam or dimethylaminoethyl methacrylate), polymers containing pyrrolidinocarbonyl aspartate groups, polyesteramides and polyvinyllactams. These polymers are often expensive, and therefore a lower concentration of polymer (perhaps 40-60% as much) is often used with the addition of a cheaper synergist to improve the performance and lower the overall cost.

Other kinetic hydrate inhibitors can further be found in:
U.S. Pat. Nos. 5,741,758 and 6,331,508, which disclose the use of various amines, including polyoxyalkyleneamines, as kinetic hydrate inhibitors;
U.S. Pat. No. 6,025,302, which discloses the use of quaternary ammonium salts of polyoxyalkyleneamines as kinetic hydrate inhibitors;
U.S. Pat. Nos. 7,214,814, 7,253,138, 7,323,609 and 7,341,617 which disclose the use of functionalized amines as kinetic hydrate inhibitors;
U.S. Pat. No. 7,968,500 which discloses the use of heat generated upon mixing polyoxyalkyleneamines with acids as a means for inhibiting hydrate formation; and
U.S. Pat. No. 8,183,185 which discloses the use various salts of amines, including polyoxyalkyleneamines, as kinetic hydrate inhibitors.

Due to the above-mentioned problems relating to cost, performance and environmental impact, a need exists for the development of alternative compounds for inhibiting and controlling the formation of gas hydrates in connection with hydrocarbon production, storage and transportation including production, drilling, completion, fracturing, stimulation and injection and reinjection operations.

SUMMARY OF THE INVENTION

The present disclosure generally provides a gas hydrate inhibitor composition containing a kinetic hydrate inhibitor, in particular a hydroxyalkylurethane, which has surprisingly been found to be effective in inhibiting the formation of gas hydrates.

In another aspect, there is provided a composition including water, a crude hydrocarbon stream including one or more lower hydrocarbons or other hydrate forming compound, and the gas hydrate inhibitor composition containing the hydroxyalkylurethane. Such a composition is a composition one would ordinarily expect to encounter in systems (i.e. fluid and/or conduit) for hydrocarbon drilling, production, storage and/or transportation, including production, drilling, completion, fracturing, stimulation and injection and re-injection operations.

In still another aspect, there is provided a method for inhibiting formation of gas hydrates that involves contacting a crude hydrocarbon stream comprising a mixture of water and one or more lower hydrocarbons or other hydrate forming compound at gas hydrate forming conditions with an amount of the gas hydrate inhibitor composition containing the hydroxyalkylurethane effective to inhibit formation of gas hydrates at the gas hydrate forming conditions.

DETAILED DESCRIPTION OF THE INVENTION

Figure 1:
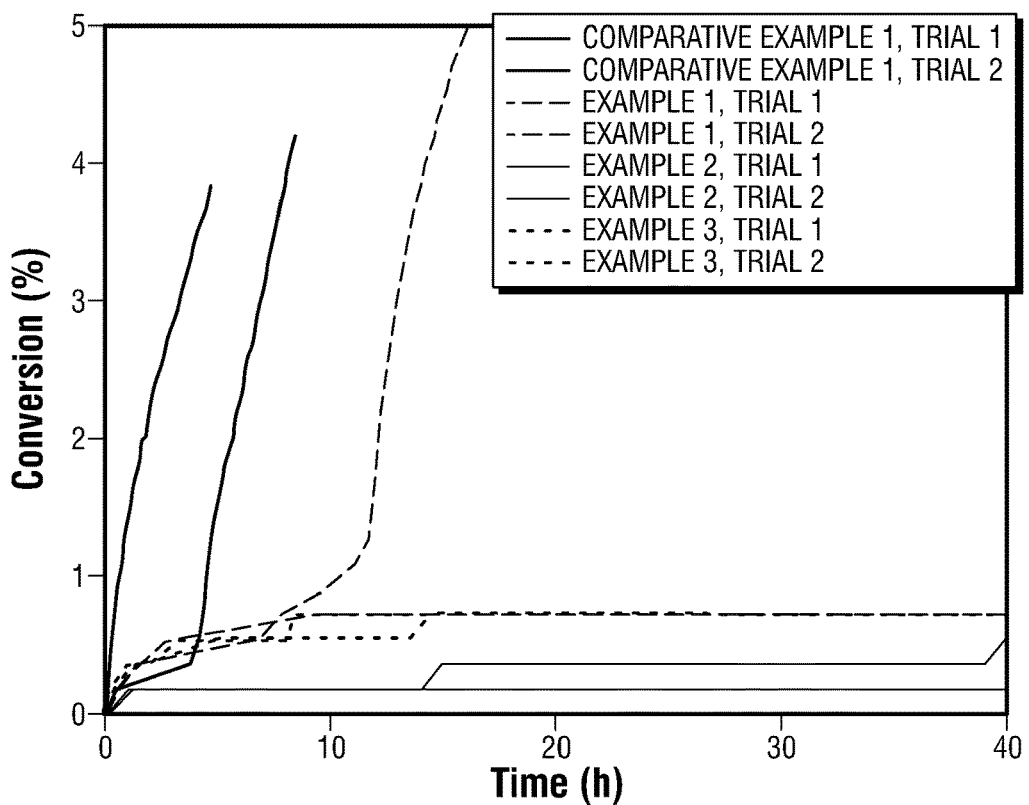
FIG. 1 depicts gas hydrate conversion (%) over time (hr) at 2° C. under a pressure of 550 psig Green Canyon gas in the presence of the hydroxyalkylurethanes of examples 1, 2 and 3 and comparative example 1.

The present disclosure is generally directed to a gas hydrate inhibitor composition including a kinetic hydrate inhibitor, and in particular, a hydroxyalkylurethane, and its use in inhibiting formation of gas hydrates in systems for hydrocarbon production, storage and transportation including production, drilling, completion, fracturing, stimulation and injection and reinjection operations.

The following terms shall have the following meanings:

The term "comprising" and derivatives thereof are not intended to exclude the presence of any additional component, step or procedure, whether or not the same is disclosed herein. In order to avoid any doubt, all compositions claimed herein through use of the term "comprising" may include any additional additive, adjuvant, or compound, unless stated to the contrary. In contrast, the term, "consisting essentially of" if appearing herein, excludes from the scope of any succeeding recitation any other component, step or procedure, except those that are not essential to operability and the term "consisting of", if used, excludes any component, step or procedure not specifically delineated or listed. The term "or", unless stated otherwise, refers to the listed members individually as well as in any combination.

The articles "a" and "an" are used herein to refer to one or to more than one (i.e. to at least one) of the grammatical objects of the article. By way of example, "an alkylene carbonate" means one alkylene carbonate or more than one alkylene carbonate. The phrases "in one aspect", "according to one aspect" and the like generally mean the particular feature, structure, or characteristic following the phrase is included in at least one aspect of the present disclosure, and may be included in more than one aspect of the present disclosure. Importantly, such phrases do not necessarily refer to the same aspect. If the specification states a component or feature "may", "can", "could", or "might" be included or have a characteristic, that particular component or feature is not required to be included or have the characteristic.

The term "inhibiting" is used herein in a broad and general sense to mean any improvement in preventing, controlling, delaying, reducing or mitigating the formation or growth of gas hydrates, particularly lower hydrocarbon gas hydrates, in any manner, including, but not limited to kinetically, thermodynamically, by dissolution, by breaking up or any combination thereof. Although the term "inhibiting" is not intended to be restricted to the complete cessation of gas hydrate formation, it may include the possibility that formation of any gas hydrate is entirely prevented.

The term "crude hydrocarbon stream" refers to an unrefined product from a natural hydrocarbon producing well, such as, for example, a methane product, a natural gas product, a crude petroleum oil product, or any mixtures thereof. Thus, in one aspect, the crude hydrocarbon stream can comprise, consist of, or consist essentially of methane. In another aspect, the crude hydrocarbon stream can comprise, consist of, or consist essentially of natural gas. In a further aspect, the crude hydrocarbon stream can comprise, consist of, or consist essentially of a condensate. In yet a further aspect, the crude hydrocarbon stream can comprise, consist of, or consist essentially of crude petroleum. In still a further aspect, the crude hydrocarbon stream can comprise, consist of, or consist essentially of a mixture of natural gas and crude petroleum, or it can comprise, consist of, or consist essentially of a mixture of methane and crude petroleum. The crude hydrocarbon stream can be heavy on gas, meaning the stream comprises more gaseous hydrocarbons than liquid hydrocarbons, or it can be heavy on oils, meaning the stream comprises more liquid hydrocarbons than gaseous hydrocarbons. In one aspect, the crude hydrocarbon stream can comprise, consist of, or consist essentially of gaseous hydrocarbons. In another aspect the crude hydrocarbon stream can comprise, consist of, or consist essentially of liquid hydrocarbons. These hydrocarbon streams can additionally comprise one or more lower hydrocarbons or other hydrate forming compound, or in some cases, two or more lower hydrocarbons or other hydrate forming compound.

As used herein the term "condensate" refers to a low-density mixture of hydrocarbon liquids that are present as gaseous components in a raw natural gas and that condenses out of the raw gas if the temperature is reduced to below the hydrocarbon dew point temperature of the raw gas.

As used herein, the term "gas hydrate" means a crystalline hydrate of a lower hydrocarbon or other hydrate forming compound including, but not limited to, carbon dioxide, hydrogen sulfide and nitrogen.

The term "lower hydrocarbon" means any of methane, ethane, propane, any isomer of butane, and any isomer of pentane.

According to one aspect, the gas hydrate inhibitor composition includes a kinetic hydrate inhibitor comprising a hydroxyalkylurethane. The hydroxyalkylurethane can be prepared by the reaction of an amine and an alkylene carbonate.

According to one aspect, the amine is a compound having the general formula $R_0-(NH_2)_n$ where $R_0$ is a linear or branched $C_2$-$C_{20}$ alkyl group or a polyoxyalkylene chain derived from ethylene oxide, propylene oxide, butylene oxide or mixtures thereof, and n is an integer from 1 to 3.

In another aspect, the amine is a compound in which $R_0$ is a linear or branched $C_2$-$C_{20}$ alky group. Examples of such amines include, but are not limited to, n-propylamine, isopropylamine, n-butylamine, isobutylamine, sec-butylamine, tert-butylamine, 3-methylbutylamine, n-hexylamine, n-octylamine, 2-ethylhexylamine, isononylamine, N,N-(di-tert-butyl)ethyleneamine, 3-(diethylamino)propylamine, 2-(diethylamino)ethyl amine, 1-methyl-4-(diethylamino)butyl amine, 2,2-(di-tert-butylamino)ethyl amine, 3-(dimethylamino)propylamine, diethylamine, di-n-propylamine, diisopropylamine, di-n-hexylamine, N-methylbutylamine, N-ethylbutylamine, di-n-butylamine, diisobutylamine, di-n-octylamine, bis(2-ethylhexyl)amine, N-ethyl-1,2-dimethylpropylamine, ethylenediamine, 1,2-propylenediamine, trimethylenedi amine, hexamethylenediamine, 2,2-dimethylpropane-1,3-diamine, 1-methyl-1,3-propanediamine, 1,2,3-trimethyl-1,4-butanediamine, 2-methyl-1,5diaminopentane, 2,2,4- or 2,4,4-trimethylhexamethylene diamine, 2,2-dimethyl-1,3-propanediamine, N,N'-di-t-butyl-ethanediamine, N,N'-dimethylhexyl-1,6-di amine, 1,6-diamino-trimethylhexane, N,N'-dimethyl-1,3-propanediamine, diethylenetriamine, N,N-dimethyldipropylenetriamine, bis(hexamethylene)triamine and mixtures thereof.

In another aspect, the amine is a compound in which $R_0$ is a polyoxyalkylene chain derived from an alkylene oxide such as ethylene oxide, propylene oxide, butylene oxide or a mixture thereof. In a further aspect, the polyoxyalkylene chain may contain 2 to 20 alkylene oxide repeating units, or 2 to 10 alkylene oxide repeating units, or even still 3 to 10 alkylene oxide repeating units. In yet another aspect, the amine compound in which $R_0$ is a polyoxyalkylene chain derived from an alkylene oxide, such as ethylene oxide, propylene oxide, butylene oxide or mixtures thereof, may also contain secondary amine-functional species, which can also react with the alkylene carbonate to give the corresponding hydroxyalkylurethanes, resulting from coupling side-reactions associated with their manufacture. Such amines in some embodiments may have the general formula

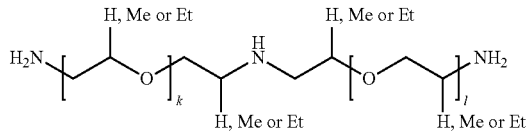

where H is hydrogen, Me is methyl, Et is ethyl and k and l are integers from 1 to 50 or in some aspects from 2 to 20.

In one particular aspect, the amine is a compound having a general formulae (1)-(8):

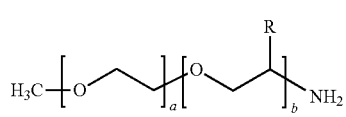
(1)

where R is hydrogen, methyl or ethyl, and
a and b independently are integers from about 1 to about 150;

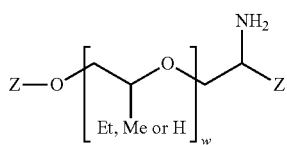
(2)

where H is hydrogen, Me is methyl and Et is ethyl,
Z is a $C_1$-$C_{40}$ alkyl group or a $C_1$-$C_{40}$ alkyl phenol group and
w is an integer from about 1 to about 100;

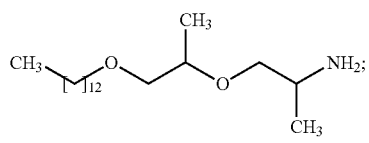
(3)

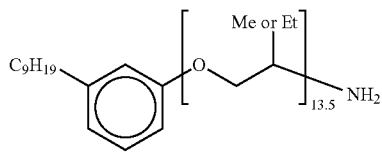
(4)

where Me is methyl and Et is ethyl;

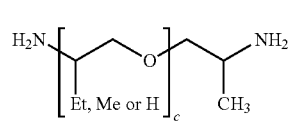
(5)

where c is an integer from about 2 to about 100, and
H is hydrogen, Me is methyl, Et is ethyl;

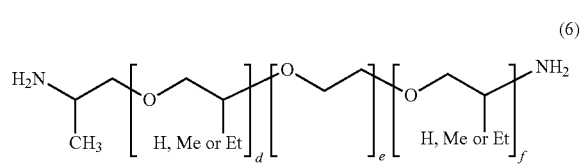
(6)

where H is hydrogen, Me is methyl, Et is ethyl,
e is an integer from about 2 to about 40, and
d and f independently are integers from about 1 to about 10;

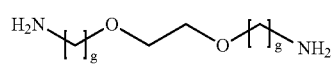
(7)

where g is an integer from about 2 to about 3; and

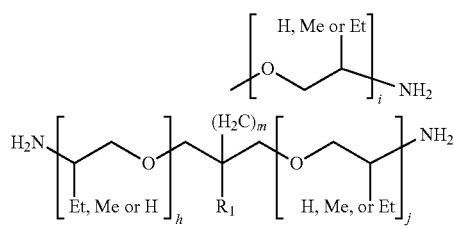
(8)

where $R_1$ is hydrogen, methyl or ethyl,
H is hydrogen, Me is methyl, Et is ethyl,
m is an integer 0 or 1, and
h, i and j independently are integers from about 1 to about 100.

Commercially available amines of formulae (1)-(4) include JEFFAMINE® M-series and XTJ-series amines, such as, but not limited to, JEFFAMINE® M-600, M-1000, M-2005, M-2070, XTJ-435 and XTJ-436 amines. Commercially available amines of formulae (5)-(7) include JEFFAMINE® D, ED and EDR amines, such as, but not limited to, JEFFAMINE® D-230, D-400, D-2000, D-4000, ED-600, ED-900, ED-20003, EDR-148 and EDR-176 amines. Commercially available amines of formula (8) include JEFFAMINE® T-series amines, such as, but not limited to, JEFFAMINE® T-403, T-3000 and T-5000 amines.

According to another aspect, the alkylene carbonate is a compound having a formula (9) or (10):

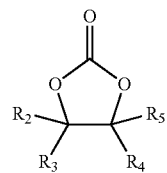

(9)

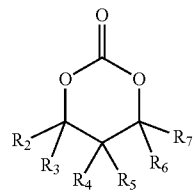

(10)

where $R_2$, $R_3$, $R_4$, $R_5$, $R_6$ and $R_7$ are the same or different and are selected from hydrogen, a $C_1$-$C_6$ alkyl and a C hydroxyalkyl.

Examples of alkylene carbonates include, but are not limited to, ethylene carbonate, 1,2-propylene carbonate, 1,2-butylene carbonate, 2,3-butylene carbonate, 1,2-pentylene carbonate, 1,2 glycerol carbonate, 4,5-dimethyl-1,3-dioxolan-2-one, 4-ethyl-1,3-dioxolan-2-one, 4,4-dimethyl-1,3-dioxolan-2-one, 4-methyl-5-ethyl-1,3-dioxolan-2-one, 4,5-diethyl-1,3-dioxolan-2-one, 4,4-diethyl-1,3-dioxolan-2-one, 1,3-dioxan-2-one, 4,4-dimethyl-1,3-dioxan-2-one, 5,5-dimethyl-1,3-dioxan-2-one, 5,5-dihydroxymethyl-1,3-dioxan-2-one, 5-methyl-1,3-dioxan-2-one, 4-methyl-1,3-dioxan-2-one; 5-hydroxy-1,3-dioxan-2-one, 5,5-diethyl-1,3-dioxan-2-one, 5-methyl-5-propyl-1,3-dioxan-2-one, 4,6-dimethyl-1,3-dioxan-2-one, 4,4,6-trimethyl-1,3-dioxan-2-one and a mixture thereof.

The hydroxyalkylurethane can be obtained by contacting the amine and alkylene carbonate and allowing them to react. The reaction may be generally represented by the reaction schemes (i) and (ii):

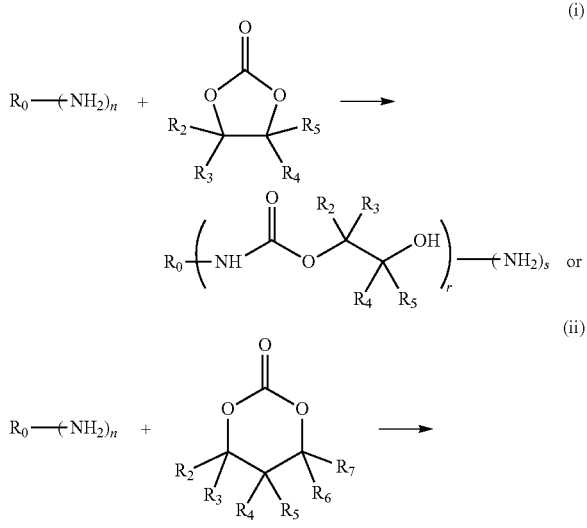

(i)

(ii)

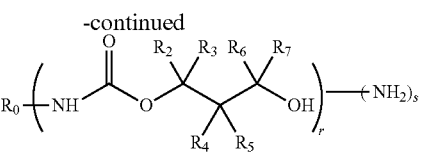

where $R_0$, $R_2$, $R_3$, $R_4$, $R_5$, $R_6$, $R_7$ and n are defined as above, r and s are integers from 1 to 3 with the proviso that r+s=n.

The reaction above may be carried out in bulk or in the presence of a solvent which is inert, that is to say it does not interfere with the reaction. The solvent may be, for example, an ether such as diethyl ether, tetrahydrofuran, dioxane, 1,2-dimethoxyethane or diethylene glycol dimethyl ether, an alcohol such as ethanol, butanol or ethylene glycol, cycloaliphatic or aromatic hydrocarbons, such as hexane, heptane, toluene or xylene and dimethylformamide or N-methylpyrrolidone.

The reaction above may also be advantageously carried out within a temperature range from 0° C. to 150° C., such as from 20° C. to 120° C., or from 30° C. to 100° C. or especially from 50° C. to 90° C.

The reaction between the amine and alkylene carbonate is generally exothermic and therefore may require the controlled metering of either the amine into the alkylene carbonate or vice versa so as to maintain a reaction temperature within the temperature ranges recited above.

Although not wishing to limit the scope of the present disclosure, the reaction may also be conducted in the presence or absence of a catalyst. Catalysts useful in accordance with the present disclosure include, but are not limited to, alkali or alkali earth metal carbonates, hydroxides or alkoxides or complexes based on titanium, aluminum, zinc or other transition metal.

In other aspects, the amine and alkylene carbonate components are allowed to react for about 0.5 hours to about 24 hours or until conversion of the amine groups is 85% or greater.

The amounts of alkylene carbonate and amine used in preparing the hydroxyalkylurethane may be varied within a wide range. For example, if the amine has one primary amino group per molecule, the molar ratio of alkylene carbonate to primary amine can be 0.5:1 to 1:0.5, especially 0.8:1 to 1:0.8. If the amine has two amine groups per molecule or three amine groups per molecule, an excess of alkylene carbonate can be used in order to avoid crosslinking, such as a molar ratio of alkylene carbonate to diamine or triamine of up to 10:1, such as from 2:1 to 5:1. In one particular aspect, the hydroxyalkylurethane may be prepared by contacting the analogous amine with between one and three molar equivalents of the alkylene carbonate.

In one aspect, the gas hydrate inhibitor composition can comprise, consist of or consist essentially of the above described hydroxyalkylurethane. In other aspects, the gas hydrate inhibitor composition can comprise the above described hydroxyalkylurethane and a second hydrate inhibitor known in the art or a solvent or an additive included for purposes other than gas hydrate inhibition.

Non-limiting examples of the second hydrate inhibitor that may be used in combination with the hydroxyalkylurethane in the gas hydrate inhibitor composition include those selected from the group of: a thermodynamic inhibitor (including, but not limited to, methanol, ethanol, n-propanol, isopropanol, ethylene glycol, propylene glycol); a kinetic hydrate inhibitor (including, but not limited to homopolymers or copolymers of vinylpyrrolidone, vinylcaprolactam, vinylpyridine, vinylformamide, N-vinyl-N-methylacetamide, acrylamide, methacrylamide, ethylacrylamide, N-methylacrylamide, N,N-dimethylacrylamide, N-ethylacrylamide, N-isopropylacrylamide, N-butylacrylamide, N-t-butylacrylamide, N-octylacrylamide, N-t-octylacrylamide, N-octadecylacrylamide, N-phenylacrylamide, N-methylmethacrylamide, N-ethylmethacrylamide, N-isopropylmethacrylamide, N-dodecylmethacrylamide, 1-vinylimidazole, and 1-vinyl-2-methylvinylimidazole); an agglomeration inhibitor (including, but not limited to, tetralkylammonium salts, tetraalkylphosphonium salts, trialkyl acyloxylalkyl ammonium salts, dialkyl diacyloxyalkyl ammonium salts, amidoamines, alkoxylated diamines, trialkyl alkyloxyalkyl ammonium salts, and trialkyl alkylpolyalkoxyalkyl ammonium salts) and a mixture thereof. The second hydrate inhibitor may be present in the gas hydrate inhibitor composition in an amount of less than 50% by weight, or less than 25% by weight, or less than 10% by weight, or less than 5% by weight, or even less than 3% by weight, based on the total weight of the gas hydrate inhibitor composition Solvents suitable for use in the gas hydrate inhibitor composition may include water, $C_4$-$C_6$ alcohols, $C_4$-$C_6$ glycols, $C_4$-$C_{10}$ ethers, $C_1$-$C_6$ mono-alkyl ethers of $C_2$-$C_6$ glycols, $C_3$-$C_6$ esters, and $C_3$-$C_6$ ketones. The solvent may be present in the gas hydrate inhibitor composition in an amount of less than 95% by weight, or less than 50% by weight, or less than 30% by weight, or less than 15% by weight, or even less than 5% by weight, based on the total weight of the gas hydrate inhibitor composition.

Additives suitable for use in the gas hydrate inhibitor composition may include polymers, amphiphiles and surfactants. These may be non-ionic or anionic. Examples include alkylpolyglycosides, hydroxylethycellulose, carboxymethylcellulose and other ionic or nonionic surfactant molecules. Other suitable additives include corrosion inhibitors, wax inhibitors, asphaltene inhibitors, biocides, demulsifiers, defoamers and scale inhibitors or any combination thereof. Additives may be present in the gas hydrate inhibitor composition in an amount of less than 20% by weight, or less than 15% by weight, or less than 10% by weight, or less than 5% by weight, or even less than 3% by weight, based on the total weight of the gas hydrate inhibitor composition.

According to one particular aspect, the gas hydrate inhibitor composition comprises at least 0.01% by weight of the above described hydroxyalkylurethane and less than 99.99% by weight of another gas hydrate inhibitor selected from the group consisting of a kinetic hydrate inhibitor, a thermodynamic inhibitor, an agglomeration inhibitor and a mixture thereof, where the % by weights are based on the total weight of the gas hydrate inhibitor composition. In other aspects, the gas hydrate inhibitor composition comprises at least 50% by weight, or at least 75% by weight, or even at least 95% by weight, or even still at least 99% by weight, yet even still at least 99.5% by weight of the above described hydroxyalkylurethane and less than 50% by weight, or less than 25% by weight, or even less than 5% by weight or even still less than 1% by weight, yet even still less than 0.5% by weight of another gas hydrate inhibitor selected from the group consisting of a kinetic hydrate inhibitor, a thermodynamic inhibitor, an agglomeration inhibitor and a mixture thereof, where the % by weights are based on the total weight of the gas hydrate inhibitor composition.

In a further aspect the present disclosure is directed to a composition containing water, a crude hydrocarbon stream, and the gas hydrate inhibitor composition of the present disclosure. Such compositions describe what one would expect to find inside conduits, for example, a crude natural gas stream and/or a crude petroleum stream pipeline and/or in equipment used to handle and process crude natural gas streams and/or crude petroleum streams.

Thus, according to one particular aspect, the composition can be made up of water, a crude hydrocarbon stream containing one or more lower hydrocarbons or other hydrate forming compound and a gas hydrate inhibitor composition comprising, consisting of, or consisting essentially of the above described hydroxyalkylurethane.

In another aspect, the composition can be made up of water, a crude natural gas stream containing one or more lower hydrocarbons or other hydrate forming compound, and a gas hydrate inhibitor composition comprising, consisting of, or consisting essentially of the above described hydroxyalkylurethane.

In still another aspect the composition can be made up of water, a crude petroleum stream containing one or more lower hydrocarbons or other hydrate forming compound, and a gas hydrate inhibitor composition comprising, consisting of, or consisting essentially of the above described hydroxyalkylurethane.

In yet still another aspect, the composition can be made up of water, a methane stream containing one or more lower hydrocarbons or other hydrate forming compound, and a gas hydrate inhibitor composition comprising, consisting of, or consisting essentially of the above described hydroxyalkylurethane.

In the foregoing aspects, the one or more lower hydrocarbons or other hydrate forming compound can include any combination of lower hydrocarbons or other hydrate forming compounds, such as, for example, methane, ethane, propane, any isomer of butane, any isomer of pentane, carbon dioxide, hydrogen sulfide, nitrogen, and combinations thereof.

The water content of such compositions may vary greatly. One benefit of the gas hydrate inhibitor composition of the present disclosure is that it is effective as a hydrate inhibitor even at relatively high water contents where other state of the art hydrate inhibitors may no longer be effective. In some aspects, the compositions described herein may contain at least 10%, by weight, water, or even at least 20%, 30%, 40%, 50%, 60%, 70%, 80% or even 90%, 95% or even 99% by weight water, based on the total weight of the composition. In other aspects, the composition may be described as having a water cut, where the water cut refers to the amount of aqueous phase present relative to the total liquids present, ignoring any gaseous phase and where the described gas hydrate inhibitor composition is considered part of the water phase. Such water cuts in the described compositions may be any of the percentages noted above, and in some aspects may be from 30% to about 100% by weight, where 100% means that essentially no oil phase is present, which may also be described as a wet gas situation (i.e. a gas pipeline containing some amount of water but no oil component).

In another aspect, the composition may also contain some amount of gas hydrates, where at least a portion of the water and at least a portion of the one or more lower hydrocarbons or other hydrate forming compound, present in the crude hydrocarbon stream, are in the form of one or more gas hydrates.

The gas hydrate inhibitor composition may be added to the composition comprising the crude hydrocarbon stream and water in an amount effective to inhibit gas hydrate formation in the overall composition. Typically, such hydrate formation occurs at elevated pressures, generally at least 0.2 MPa, or even at least 0.5 MPa, and even at least 1.0 MPa. The gas hydrate inhibitor composition may be added to the composition containing the crude hydrocarbon stream before water is added, or vice versa, or it may be added to a composition already containing both. The addition may be performed before or after the composition is subjected to elevated pressures or to reduced temperatures.

It will be appreciated that it is very difficult, if not impossible, to predict a priori the dosage or proportion of gas hydrate inhibitor composition that will be effective in inhibiting gas hydrate formation in a given application. There are a number of complex, interrelated factors that must be taken into account, including, but not limited to, the salinity of the water, the composition of the crude hydrocarbon stream, the relative amounts of water and crude hydrocarbon stream, and the temperature and pressure. For these reasons, the dosage and proportion of the gas hydrate inhibitor composition may be generally optimized through laboratory and field testing for a given application, using techniques well known to those of ordinary skill in the art. Exemplary non-limiting gas hydrate inhibitor composition use concentrations, calculated as 100% of active substance, may be from about 0.005% by weight to about 8% by weight, for instance, or from about 0.0075% by weight to about 5% by weight, or especially from about 0.01% by weight to about 3% by weight and even concentrations of from about 0.02% by weight to about 1% by weight (100-10,000 ppm), based on the total weight of water in the composition.

Another aspect of the present disclosure is directed to a method of inhibiting gas hydrate formation, where the method includes contacting a crude hydrocarbon stream, itself made up of water and one or more lower hydrocarbons or other hydrate forming compound, with the above described gas hydrate inhibitor composition containing the above described hydroxyalkylurethane. Thus, in one aspect the method includes contacting a crude hydrocarbon stream comprising water and one or more lower hydrocarbons or other hydrate forming compound with the gas hydrate inhibitor composition comprising an above described hydroxyalkylurethane.

The contacting of the gas hydrate inhibitor compositions herein with the crude hydrocarbon stream may be achieved by a number of ways or techniques, including, but not necessarily limited to, mixing, blending with mechanical mixing equipment or devices, static mixers, magnetic mixing or other suitable methods, other equipment and means known to one skilled in the art and combinations thereof to provide adequate contact and/or dispersion of the gas hydrate inhibitor composition in the crude hydrocarbon stream. The contacting can be made in-line or off-line or both.

In one particular aspect, contacting can occur when the gas hydrate inhibitor composition is injected into a downhole location in a producing well to inhibit gas hydrate formation in a crude hydrocarbon stream being produced through the well. Likewise, the gas hydrate inhibitor composition may be injected into the crude hydrocarbon stream at a wellhead location, or even into piping extending through a riser, through which the crude hydrocarbon stream is being transported in offshore producing operations from the ocean floor to the offshore producing facility located at or above the surface of the water. Additionally, the gas hydrate inhibitor may be injected into a crude hydrocarbon stream prior to transporting, for example via a subsea pipeline from an offshore producing location to an onshore gathering and/or processing facility.

In another particular aspect, contacting of the gas hydrate inhibitor composition and the crude hydrocarbon stream is aided by mechanical means well known in the art, including for example the use of a static in-line mixer in a pipeline. In most pipeline transportation applications, however, sufficient contacting will occur due to the turbulent nature of the fluid flow, and mechanical mixing aids are not necessary.

The temperature of the condition for contacting is usually below, the same as, or not much higher than, ambient or room temperature. Lower temperatures tend to favor gas hydrate formation, thus requiring the treatment with the gas hydrate inhibitor compositions described herein. At much higher temperatures however, gas hydrates may not form, thus obviating the need of carrying out any treatments.

The pressure at which the gas hydrate inhibitor composition and crude hydrocarbon stream are contacted is usually at or greater than atmospheric pressure, (i.e. about 101 kPa), or greater than about 1 MPa, and even greater than about 5 MPa. The pressure in certain formation or processing plants or units could be much higher, for example greater than about 20 MPa. There is no specific high-pressure limit. The method can be used at any pressure that allows formation of gas hydrates.

As discussed above, the amount of gas hydrate inhibitor composition required to effectively inhibit gas hydrate formation in any particular crude hydrocarbon stream will depend upon the composition of that stream and the conditions of temperature and pressure to which the fluid mixture will be subjected. Generally, however, the hydrate inhibitor will be added to the fluid mixture in the amounts described above, or in other aspects in an amount of from about 0.01% by weight to about 5% by weight, or from about 0.1% by weight to about 1% by weight of the water present in the gas hydrate inhibitor composition and crude hydrocarbon stream mixture.

If needed or desired in some aspects, the gas hydrate inhibitor composition or some of its components may be optionally removed or separated from the crude hydrocarbon stream mechanically, chemically, or by other methods known to one skilled in the art, or by a combination of these methods after the gas hydrate formation conditions are no longer present.

The present disclosure will now be further described with reference to the following non-limiting examples.

EXAMPLES

Examples 1-7. Preparation of Hydroxyalkylurethanes

Hydroxyalkylurethanes were prepared by slowly adding an alkylene carbonate to a polyoxyalkyleneamine with stirring. Homogenized mixtures were then stored in an oven set to 90° C. for 16 hours, then allowed to cool. Details for each example are given below in Table 1.

Aqueous solutions of the hydroxyalkylurethanes were then subsequently prepared to test their hydrate inhibitor performance. Results were evaluated relative to comparative examples C1, C2 and C3 which consisted of 11 mM aqueous solutions of JEFFAMINE® D-230 amine (0.250% by wt.), JEFFAMINE® EDR-148 amine (0.163% by wt.) and JEFFAMINE® T-403 amine (0.478% by wt.). Each of the hydroxyalkylurethane solutions tested was also made to a concentration of 11 mM. Corresponding % by wt. values are also provided below in Table 1.

TABLE 1

| Example | Amine [1] | Alkylene Carbonate [2] | Molar Ratio [3] | Conc. [4] (% by weight) |
|---|---|---|---|---|
| C1 [5] | D-230 | — | — | 0.250 |
| C2 [5] | EDR-148 | — | — | 0.163 |
| C3 [5] | T-403 | — | — | 0.478 |
| 1 | D-230 | PC | 1:1 | 0.365 |
| 2 | D-230 | PC | 1:2 | 0.477 |
| 3 | D-230 | BC | 1:1 | 0.381 |
| 4 | D-230 | BC | 1:2 | 0.508 |
| 5 | EDR-148 | PC | 1:2 | 0.387 |
| 6 | T-403 | PC | 1:3 | 0.821 |
| 7 | T-403 | BC | 1:1.5 [6] | 0.667 |

[1] D-230 = JEFFAMINE ® D-230, poly(propylene oxide) diamine, MW ~230; EDR-148 = JEFFAMINE ® EDR-148, triethylene glycol diamine; T-403 = JEFFAMINE ® T-403, poly(propylene oxide) triamine based on methylolpropane, MW ~440.
[2] PC = JEFFSOL ® propylene carbonate, where $R_2$ = $CH_3$ and $R_3$-$R_5$ = H in reaction (i) above; BC = JEFFSOL ® butylene carbonate, where $R_2$ = $C_2H_5$ and $R_3$-$R_5$ = H in reaction (i) above.
[3] Molar ratio of polyoxyalkyleneamine to alkylene carbonate employed.
[4] Concentration of hydroxyalkylurethane based on the total wt. of the aq. test solution.
[5] Comparative examples 1, 2 and 3.
[6] Hydroxyalkylurethane made from T-403 and BC with molar ratios in excess of 1:1.5 was only sparingly water soluble.

Gas hydrate conversation rate experiments were performed in a custom-built 500-mL volume, 100 Bar pressure-rated testing cell. Gas pressure, temperature, stirring speed and torque power were controlled and continuously recorded. Prior to testing, the cell was charged with the fluid to be tested and pressurized to ~50 psi with test gas. The fluid was then heated to 40°-45° C. with stirring and maintained at that temperature for six hours to rinse the cell. The fluid was then drained and the cell charged with new test fluid. The cell was then pressurized with gas and cooled to the desired pressure-temperature conditions. Occasionally, a minor adjustment to the pressure was necessary upon completion of this step. The fluid was then maintained at constant temperature until gas hydrate conversion, defined as $100 \times [1-(p_f/p_i)]$, where $p_f$ and $p_i$ are the final and initial pressures, respectively, reached 10%. A stirring speed of 250 rpm was maintained throughout the procedure. Upon completion of the test, the fluid was warmed to 40°-45° C. and maintained at that temperature for six hours to completely melt the hydrates formed during the test. The fluid was then cooled to the same initial pressure-temperature conditions employed above and duplicate tests were conducted in the same manner as the first.

Each aq. test solution was monitored for gas hydrate formation in the presence of Green Canyon gas (87.2 mol % methane, 7.6 mol % ethane, 3.1 mol % propane, 0.8 mol % n-butane, 0.5 mol % isobutene, 0.4 mol % nitrogen, 0.2 mol % isopentane, 0.2 mol % n-pentane) at an initial pressure of ~550 psi and a temperature of 2° C. (12° C. sub-cooling). The % hydrate conversion, calculated as detailed above, was plotted as a function of time in hours. The performance of each solution was measured at least two times.

Kinetic hydrate inhibitor performance measured in terms of the time in hours required to reach hydrate conversions of 0.5% (widely referred to in the industry as the induction time), 3% and 5% at 2° C. under 550 psig Green Canyon gas is provided in Table 2.

TABLE 2

| Example | Trial No. | Hydrate Conv. (hr) 0.5% | 3% | 5% |
|---|---|---|---|---|
| C1 | 1 | <1 | 3.4 | —[1] |
| C1 | 2 | 4.1 | 7.0 | —[1] |
| C2 | 1 | 3.2 | 3.7 | 4.1 |
| C2 | 2 | 10.9 | 11.5 | 12.0 |
| C3 | 1 | <1 | 3.1 | 7.4 |
| C3 | 2 | <1 | 0.9 | 1.6 |
| 1 | 1 | 2.8 | >92[1] | —[1] |
| 1 | 2 | 6.8 | 13.0 | 16.2 |
| 2 | 1 | 48.1 | 52.4 | —[1] |
| 2 | 2 | 39.9 | 49.2 | 51.1 |
| 3 | 1 | 5.0 | >26[1] | —[1] |
| 3 | 2 | 8.0 | >62[1] | —[1] |
| 4 | 1 | 1.1 | 5.0 | 11.8 |
| 4 | 2 | 12.5 | 14.8 | 15.9 |
| 5 | 1 | 9.0 | >56[1] | —[1] |
| 5 | 2 | 9.2 | >70[1] | —[1] |
| 6 | 1 | <1 | 3.0 | 8.2 |
| 6 | 2 | 1.2 | 7.7 | 13.9 |
| 7 | 1 | 64 | >65[1] | —[1] |
| 7 | 2 | 56 | >64[1] | —[1] |

[1]Test terminated prior to reaching hydrate conversion level.

Figure 2:
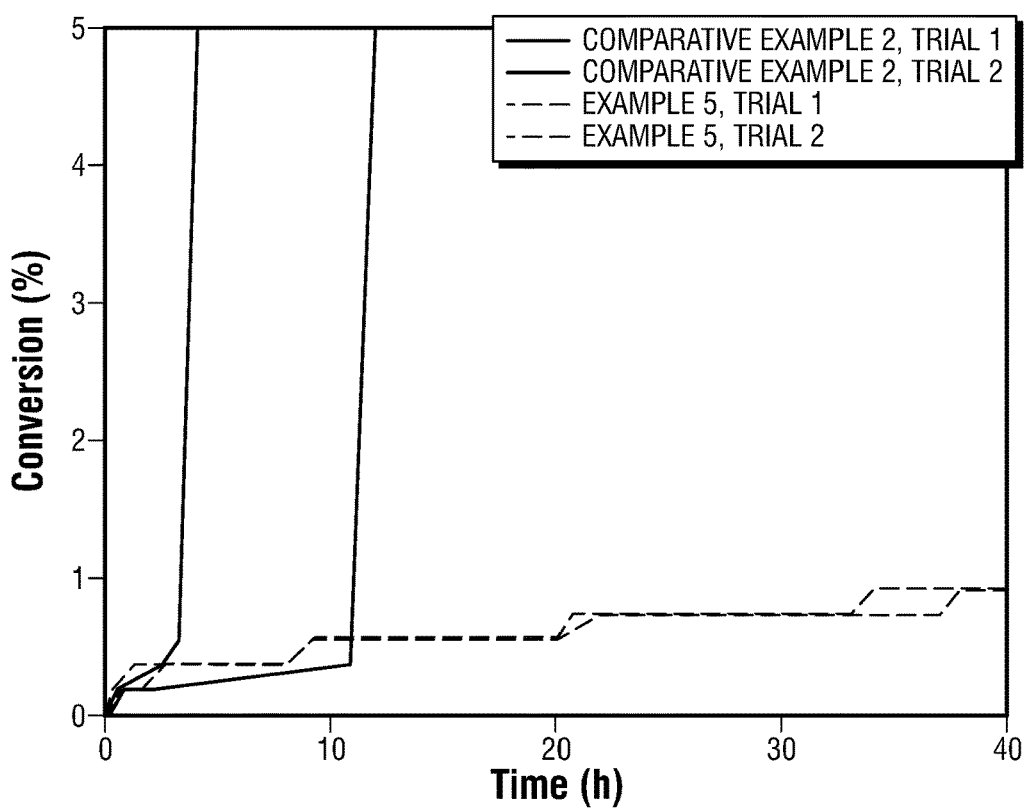
FIG. 2 depicts gas hydrate conversion (%) over time (hr) at 2° C. under a pressure of 550 psig Green Canyon gas in the presence of the hydroxyalkylurethane of example 5 and comparative example 2.
Figure 3:
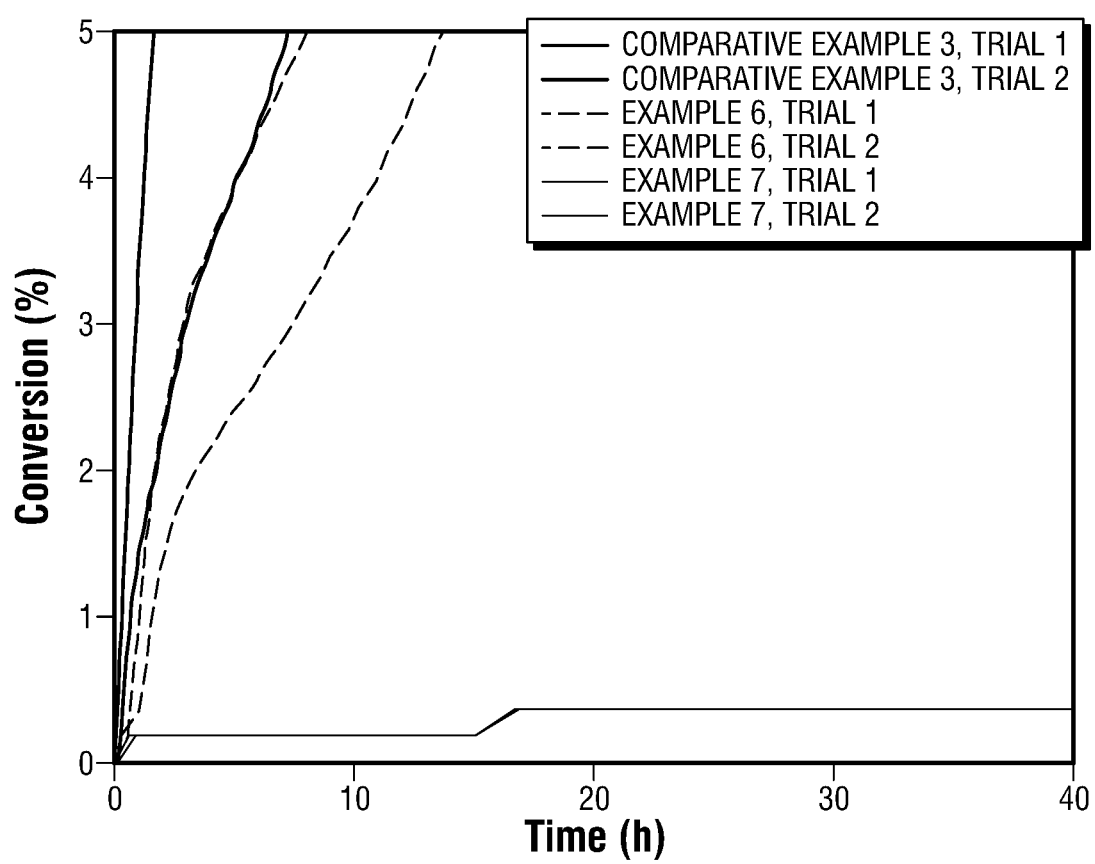
FIG. 3 depicts gas hydrate conversion (%) over time (hr) at 2° C. under a pressure of 550 psig Green Canyon gas in the presence of the hydroxyalkylurethanes of examples 6 and 7 and comparative example 3.

Although there are variations between different trials of the same example solutions, due in part to the inherent stochastic nature of hydrate crystal formation, it is clear that macroscopic hydrate formation occurs significantly more slowly in each of the inventive example solutions 1-7 than in the comparative amine solutions C1, C2 and C3. These results are shown graphically in FIGS. 1-3.

From the results above, it is shown that the inventive hydroxyalkylurethanes are more effective gas hydrate inhibitors than their amine precursors which are widely known for their kinetic hydrate inhibitor properties. That is to say, it is shown that mixtures of natural gas and water will form potentially hazardous, well- and pipeline-blocking gas hydrates more slowly under identical conditions of pressure and temperature when in the presence of the hydroxyalkylurethanes of the present disclosure than when in the presence of the corresponding amines from which the hydroxyalkylurethanes were synthesized. Although not experimentally determined herein, it is also believed that the hydroxyalkylurethanes of the present disclosure are less hazardous both to humans and the environment than the corresponding amines which said hydroxyalkyurethanes were synthesized.

Example 8

A model hydroxyalkylurethane reaction was studied using 1.4 equivalents of 1,2-propanediamine (PDA) mixed with 1.0 equivalents of JEFF SOL® propylene carbonate (PC) according to the reaction scheme (iii) below. The reaction was followed via GC/MS. Samples were injected into a Trace GC Ultra (Thermoscientific) equipped with an Agilent DB-17 polysiloxane column preheated to 50° C. using a 200:1 splitting ratio. The column temperature was held at 50° C. for 2 minutes, then increased to 280° C. at a rate of 12° C./minute. Eluted compounds were then analyzed using a DSQ II (Thermoscientific) mass spectrometer. After 72 hours at ambient temperature, products I and II constituted 53.2 and 0.7 area %, respectively. After 16 hrs. at 90° C., these products constituted 68.6 and 7.8 area %, with reactants PDA and PC constituting 18.8 and 0.8 area %.

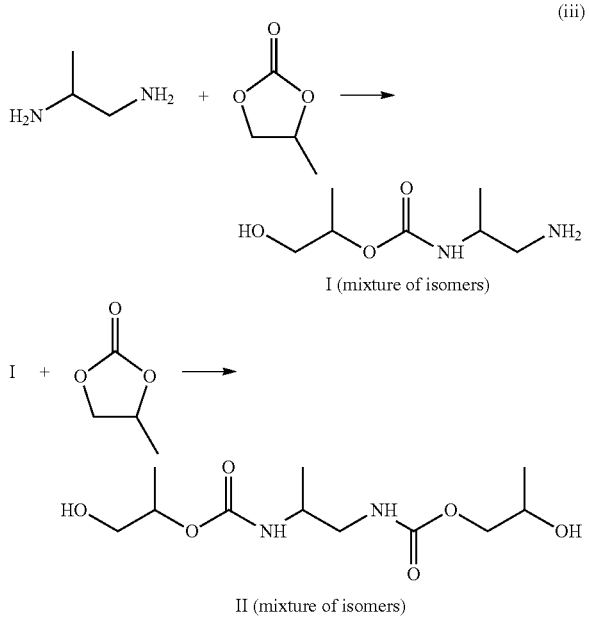

I (mixture of isomers)

II (mixture of isomers)

Although making and using various embodiments of the present invention have been described in detail above, it should be appreciated that the present invention provides many applicable inventive concepts that can be embodied in a wide variety of specific contexts. The specific embodiments discussed herein are merely illustrative of specific ways to make and use the invention, and do not delimit the scope of the invention.

What is claimed is:

1. A composition comprising water, a crude hydrocarbon stream and a gas hydrate inhibitor composition comprising at least 99.5% by weight, based on the total weight of the gas hydrate inhibitor composition, of a hydroxyalkylurethane obtained by the reaction of an amine and an alkylene carbonate.

2. The composition of claim 1, wherein the amine is a compound having the formula $R_0—(NH_2)_n$ where $R_0$ is a linear or branched $C_2$-$C_{20}$ alkyl group or a polyoxyalkylene chain derived from ethylene oxide, propylene oxide, butylene oxide or a mixture thereof, and n is an integer from 1 to 3.

3. The composition of claim 1, wherein the alkylene carbonate is a compound having a formula (9) or (10):

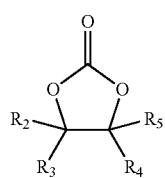

(9)

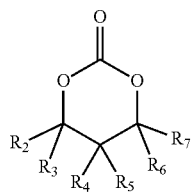

(10)

where $R_2$, $R_3$, $R_4$, $R_5$, $R_6$ and $R_7$ are the same or different and are selected from hydrogen, a $C_1$-$C_6$ alkyl and a $C_1$-$C_6$ hydroxyalkyl.

4. The composition of claim 1, wherein the crude hydrocarbon stream is a crude natural gas stream.

5. The composition of claim 1, wherein the crude hydrocarbon stream is a crude petroleum stream.

6. The composition of claim 1, wherein the gas hydrate inhibitor composition further comprises a second hydrate inhibitor or a solvent or an additive included for purposes other than gas hydrate inhibition.

7. The composition of claim 1, wherein the hydroxyalkylurethane is present in an amount of from about 0.005% by weight to about 8% by weight, based on the total weight of water in the composition.

8. A gas hydrate inhibitor composition comprising a kinetic hydrate inhibitor wherein the kinetic hydrate inhibitor is a hydroxyalkylurethane obtained by the reaction of

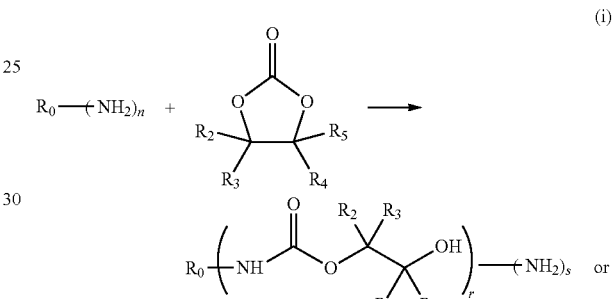

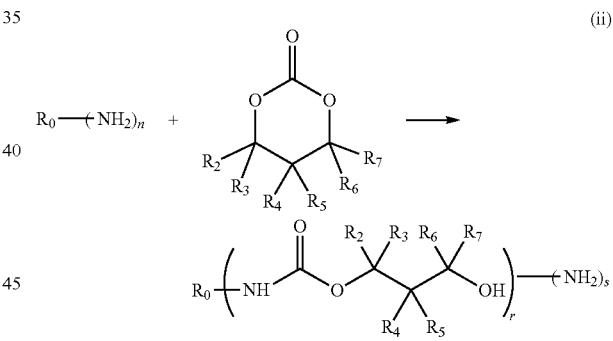

where $R_0$ is a linear or branched $C_2$-$C_{20}$ alkyl group or a polyoxyalkylene chain derived from ethylene oxide, propylene oxide, butylene oxide or a mixture thereof, $R_2$, $R_3$, $R_4$, $R_5$, $R_6$, $R_7$ are the same or different and are selected from hydrogen, a $C_1$-$C_6$ alkyl and a $C_1$-$C_6$ hydroxyalkyl, n is an integer from 1 to 3 and r and s are integers from 1 to 3 with the proviso that r+s=n.

9. The gas hydrate inhibitor composition of claim 8, further comprising a second hydrate inhibitor or a solvent or an additive included for purposes other than gas hydrate inhibition.

10. The gas hydrate inhibitor composition of claim 9, wherein the second hydrate inhibitor is selected from the group consisting of: a thermodynamic inhibitor, a kinetic hydrate inhibitor, an agglomeration inhibitor and a mixture thereof.

11. A composition comprising water, a crude hydrocarbon stream and a gas hydrate inhibitor composition comprising a hydroxyalkylurethane obtained by the reaction of

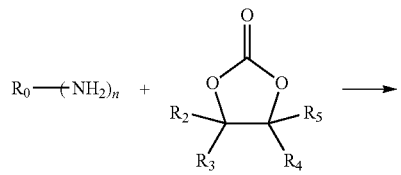
(i)

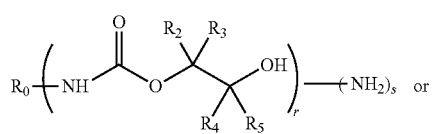
or

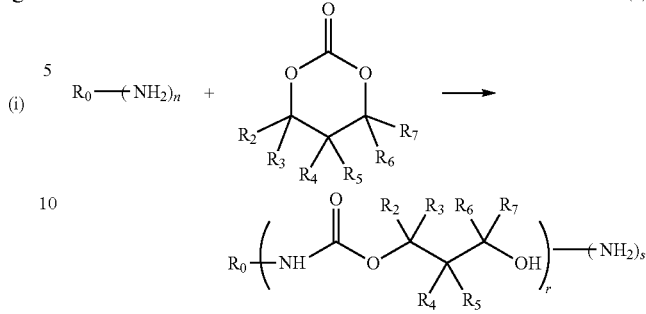
(ii)

where $R_0$ is a linear or branched $C_2$-$C_{20}$ alkyl group or a polyoxyalkylene chain derived from ethylene oxide, propylene oxide, butylene oxide or a mixture thereof,
$R_2$, $R_3$, $R_4$, $R_5$, $R_6$, $R_7$ are the same or different and are selected from hydrogen, a $C_1$-$C_6$ alkyl and a $C_1$-$C_6$ hydroxyalkyl,
n is an integer from 1 to 3 and
r and s are integers from 1 to 3 with the proviso that r+s=n.

* * * * *